(12) United States Patent
Rizo et al.

(10) Patent No.: US 11,002,680 B2
(45) Date of Patent: May 11, 2021

(54) FLUORESCENCE IMAGING SYSTEM FOR AN OPERATING ROOM

(71) Applicant: FLUOPTICS, Grenoble (FR)

(72) Inventors: Philippe Rizo, La Tronche (FR); Norman Mangeret, Jarrie (FR)

(73) Assignee: FLUOPTICS, Grenoble (FR)

( * ) Notice: Subject to any disclaimer, the term of this patent is extended or adjusted under 35 U.S.C. 154(b) by 0 days.

(21) Appl. No.: 17/077,109

(22) Filed: Oct. 22, 2020

(65) Prior Publication Data
US 2021/0055225 A1  Feb. 25, 2021

Related U.S. Application Data

(63) Continuation of application No. 14/396,381, filed as application No. PCT/EP2013/058352 on Apr. 23, 2013, now abandoned.

(30) Foreign Application Priority Data

Apr. 25, 2012 (FR) ...................................... 1253786

(51) Int. Cl.
*G01N 21/64* (2006.01)
*A61B 5/00* (2006.01)
(Continued)

(52) U.S. Cl.
CPC ....... *G01N 21/6486* (2013.01); *A61B 5/0071* (2013.01); *A61B 90/361* (2016.02); *G01N 21/6456* (2013.01); *A61B 2090/309* (2016.02); *A61B 2090/395* (2016.02); *A61B 2090/3941* (2016.02); *G01N 2021/6439* (2013.01);
(Continued)

(58) Field of Classification Search
USPC ...................................................... 250/363.01
See application file for complete search history.

(56) References Cited

U.S. PATENT DOCUMENTS 8,502,168 B1 *  8/2013  Poteet ................... G01J 3/4406
                                                           250/461.1
2012/0057226 A1 *  3/2012  Kuster ................... A61B 90/20
                                                           359/376

FOREIGN PATENT DOCUMENTS

EP          2071322 A1     6/2009

OTHER PUBLICATIONS

U.S. Appl. No. 14/396,381, filed Oct. 22, 2014.
(Continued)

*Primary Examiner* — David P Porta
*Assistant Examiner* — Carolyn Fin
(74) *Attorney, Agent, or Firm* — Occhiuti & Rohlicek LLP

(57) ABSTRACT

Fluorescence imaging system for an operating theatre, comprising a device illuminating the operating theatre and emitting a white light, and a fluorescence imaging device. Said fluorescence imaging device comprises a light source emitting radiation for excitation of a fluorescent marker in a range of emission wavelengths of between 600 and 900 nm. The light emitted by the illuminating device is filtered by a low-pass filter, of which the cut-off wavelength is below the emission range of the fluorescent marker, but is nonetheless able to show an increase or fluctuations in the attenuation for wavelengths above the emission range of the fluorescent marker, the product of the attenuation of the filter of the detector and of the attenuation of the low-pass filter of the illuminating device leading to an attenuation by a factor of at least $10^6$.

15 Claims, 10 Drawing Sheets

(51) Int. Cl.
　　　A61B 90/00　　　(2016.01)
　　　A61B 90/30　　　(2016.01)
(52) U.S. Cl.
　　　CPC ............... *G01N 2021/6471* (2013.01); *G01N 2201/062* (2013.01)

(56) References Cited

OTHER PUBLICATIONS

Gioux, S. et al., "Image-Guided Surgery Using Invisible Near-Infrared Light: Fundamentals of Clinical Translation," NIH Public Access Author Manuscript, Oct. 1, 2010, XP055046858, pp. 1-31.
Mieog, J.S.D. et al., "Toward Optimization of Imaging System and Lymphatic Tracer for Near-Infrared Fluorescent Sentinel Lymph Node Mapping Breast Cancer," Annals of Surgical Oncology, vol. 18, No. 9, Mar. 1, 2011, XP019945153, pp. 2483-2491.
Themelis G., et al., "Real-Time Intraoperative Fluorescence Imaging System using Light Absorption Correction," Journal of Biomedical Optics, vol. 14, No. 6, Nov./Dec. 2009, 9 pages.
Troyan, S.L., et al., The Flare™ Intraoperative Near-Infrared Fluorescence Imaging System. A First-in-Human Clinical Trial in Breast Cancer Sentinel Lymph Node Mapping, Annals of Surgical Oncology, Vo. 16, No. 10, Oct. 2009, pp. 2943-2952.

\* cited by examiner

-- Prior Art --

-- Prior Art --

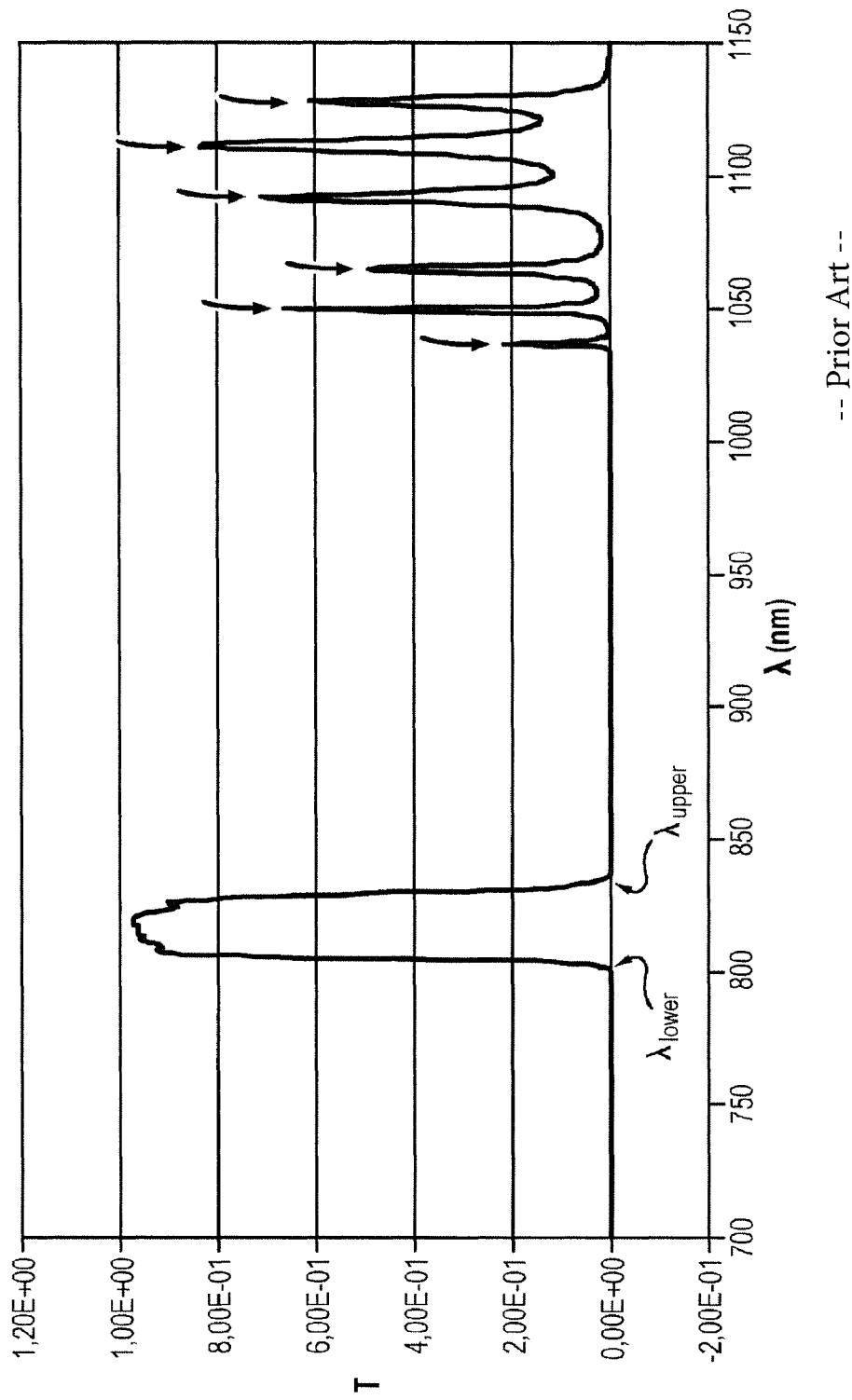
FIG. 7A -- Prior Art --

-- Prior Art --

FLUORESCENCE IMAGING SYSTEM FOR AN OPERATING ROOM

CROSS-REFERENCE TO RELATED APPLICATIONS

This application is a continuation of U.S. application Ser. No. 14/396,381, filed on Oct. 22, 2014, which is a U.S. National Phase Application of International Application No. PCT/EP2013/058352, filed on Apr. 23, 2013, which claims the benefit of the Apr. 25, 2012 priority date of French application No. 1253786, each of which is incorporated herein by reference.

FIELD OF THE INVENTION

The present invention concerns a fluorescence imaging system for an operating room comprising a device illuminating the operating room and a fluorescence medical imaging device.

BACKGROUND OF THE INVENTION

Fluorescence medical imaging is a promising technique in particular for surgical procedures for the purpose of guiding a surgeon's action.

This technique is based on administering a substance to a patient that contains a fluorescent marker e.g., for observation of a target organ or tissue that is to undergo surgical procedure or for observation of a flow monitored by the marker.

By means of the presence of the fluorescent marker in or close to the target organ or tissue, the illumination of the region of the patient comprising the organ has the effect of exciting the marker, which in turn emits radiation at a wavelength slightly longer than the excitation wavelength.

The chief applications are in the Near InfraRed (NIR) i.e. the excitation radiation and the fluorescence radiation lie in a wavelength range of between 700 and 900 nm. Once detected, the fluorescent radiation can be superimposed over an image of the organ concerned to view the target organ or tissue in relation to the outer visible portion of the organ.

The principle of fluorescence imaging is schematically illustrated in FIG. 1.

The imaging device I comprises a light source S intended to excite the fluorescent marker located in a region O of which it is desired to obtain images (the marker possibly being concentrated in this region or passing therethrough in a flow) the radiation $L_S$ provided by the light source having the effect of making the marker fluorescent.

In medical applications, the region O is generally located underneath the patient's skin P.

It is made fluorescent by administering, to the patient, a substance containing a fluorescent marker so that the marker concentrates in or passes through the region O, and by exciting the marker via radiation emitted by the light source S.

The device I also comprises a detector D adapted to detect and record the fluorescent radiation $L_F$ emitted by the marker located in the region O and excited by the source S.

For example, the detector comprises a CCD camera.

For this purpose, the light source S is filtered (filter $F_s$) so as to excite the fluorescent marker with radiation $L_E$ not containing wavelengths corresponding to the fluorescence to be measured.

For example, when the fluorescence to be measured is in the near infrared (i.e. in a wavelength range of between 700 and 900 nm) it is necessary fully to eliminate the wavelengths in the fluorescence range, not only in the excitation radiation but also in ambient light.

If not, these wavelengths would be detected by the detector D and would generate noise on the fluorescence image, harming the quality thereof.

Upstream of the detector D, the device comprises a filter $F_D$ adapted so as only to allow those photons $L_F$ to pass towards the detector whose wavelength is the fluorescence wavelength.

For fluorescence in the near infrared, the filter $F_D$ is generally a high-pass filter which transmits all the wavelengths above a given threshold.

FIG. 2 illustrates the filtering principle of such a fluorescence imaging device and gives the transmission curves T as a function of the wavelength $\lambda$ for ambient light (curve $f_A$), the excitation light source (curve $f_E$), and the detector (curve $f_D$).

In the example illustrated in this Figure, the excitation wavelength is 780 nm, ambient light is filtered so as essentially to contain wavelengths between 400 and 750 nm, while the detector is filtered so as to receive all wavelengths longer than about 820 nm.

During a surgical procedure, the patient is installed on a table in the operating room and the region to be operated is illuminated with specific lighting device present in the room.

Such a lighting device is typically a "surgical luminaire" in the form of a dome-shaped light-head carried by an arm and oriented in the direction of the patient so as to avoid any shadow area.

The fluorescence imaging device described above is also installed in the operating room and positioned for adequate viewing of the region in the patient of which it is desired to images and to detect the fluorescence emitted by this region.

The excitation light source can be fixed to the surgical luminaire itself, for example using a suitable attachment system.

On account of its very strong power (typically between 40 and 150 kLux), the lighting in the operating room may perturb detection of fluorescence radiation by producing photons that are detected by the detector.

So as not to deteriorate the quality of the fluorescence image, the light provided by the surgical luminaire must be filtered so that it does not contain wavelengths corresponding to the fluorescence to be measured.

Yet at 150 kLux, even a very slight leakage of light from the operating room lighting in the range of wavelengths measured by the detector through its filter is able to limit the quality of fluorescence images.

In addition, requirements in terms of quality of surgical lighting are drastic.

In this respect, standard NF EN 60601-2-41 can be cited concerning the particular safety rules for surgical luminaires and diagnostic lighting.

For example, the emitted light is white light which must have a color temperature generally between 3000 K and 6700 K.

It is additionally stipulated in the standard that the color rendering index (CRI) must be between 85 and 100%, preferably on the order of 95%.

As a result, the filtering of the light emitted by the surgical luminaire must not lead to degradation of the aforementioned characteristics.

Also, on account of the large surface area to be filtered for a surgical luminaire (in the order 0.5 m$^2$), it is necessary to design a low-cost filter.

Fluorescence imaging devices have already been described to guide surgical procedures.

Some systems overcome the influence of white light by switching off the surgical luminaire when conducting fluorescence imaging.

However, having to switch off the light is not conducive to a surgical procedure.

Other fluorescence imaging devices have been designed to provide continuous lighting.

For use in an operating room, the white light emitted by the surgical luminaire or the imaging device is filtered on and after the excitation wavelength so as not to contain photons of longer wavelength than the excitation wavelength, which may be 670 or 760 nm.

The fluorescence detector at 700 nm is filtered with a band-pass filter of 689 to 725 nm, whilst the detector of fluorescence at 800 nm is filtered with a band-pass filter of 800 to 848 nm.

These band-pass filters are intended only to allow detection of wavelengths corresponding to the fluorescence signal, eliminating longer wavelengths.

In at least one device, a single detector is intended to detect the fluorescence wavelengths around 700 nm and 800 nm.

The detector is filtered by a dual band-pass filter with a first bandwidth of between 689 and 725 nm, and a second bandwidth of between 803 and 853 nm.

The excitation light source is a laser diode at a wavelength of 750 nm, whilst the lighting of the operating room is provided by a halogen lamp emitting white light.

A band-pass filter is positioned upstream of the detector to prevent transmission thereto of wavelengths longer than the fluorescence wavelength.

However, with all the above-described devices, a fluorescent background can be seen in the images obtained which reduces the contrast with the fluorescence emitted by the organ or tissue of interest.

SUMMARY

The inventors generally attribute this fluorescent background to tissue autofluorescence.

However, for the wavelengths of the near infrared under consideration, autofluorescence is negligible and cannot alone account for the observed fluorescent background.

Another hypothesis to explain this unsatisfactory quality of images could be insufficient filtering of the excitation light source.

At all events, there exists a need to improve the quality of fluorescence images in the setting of an operating room.

It is therefore one objective of the invention to provide a lighting and filtering system for operating room adapted for application of fluorescence, imaging, and that, in particular, allows optimized quality of a fluorescence image even in the presence of intense continuous illumination of the surgical field.

A further objective of the invention is a filtering system that can easily be adapted to existing lighting equipment in an operating room and at moderate cost.

BRIEF DESCRIPTION OF THE INVENTION

For this purpose, a fluorescence imaging is proposed for operating room comprising an operating room illuminating device capable of emitting white light and a fluorescence imaging device;

said fluorescence imaging device comprising:
a light source capable of emitting radiation to excite a fluorescent marker in a wavelength emission range of between 600 and 900 nm;
a detector adapted to detect the fluorescent radiation emitted by the marker under the effect of excitation by the light source;
a filter for the detector adapted to attenuate the excitation radiation and to transmit those photons to the detector which have a wavelength included in the range of fluorescent radiation wavelengths emitted by the marker;
the light emitted by the illuminating device being filtered by a low-pass filter of which the cut-off wavelength is below the emission range of the fluorescent marker, said low-pass filter nonetheless being able to exhibit attenuation peaking or fluctuations at wavelengths above the emission range of the fluorescent marker.

According to the invention, in a range of wavelengths extending from an upper cut-off wavelength of the detector filter that is below the wavelength on and after which attenuation peaking or fluctuations of the low-pass filter of the illuminating device are observed, the product of the attenuation of the detector filter and of the attenuation of the low-pass filter of the illuminating device leads to an attenuation by a factor of at least $10^6$.

Herein the term «filter» may encompass an elementary filter or a combination of filters.

As explained in detail below, the effect of this filtering of the detector is to eliminate bias and background noise due to peaking of the low-pass filter of the illuminating device which, due to the intensity of operating room lighting, allows parasitic light to pass that is sufficiently intense to mask some of the fluorescence photons derived from deep regions and which are therefore few in number.

By means of this filtering, the detector becomes more sensitive to the fluorescence signal emitted from the deep layers and produces more contrasted images.

Also, since this filtering is applied to the detector which has a small surface area, it has no resultant effect on the cost of the system According to one embodiment of the invention, the wavelength of excitation radiation is between 630 and 810 nm.

Preferably, the bandwidth in which the detector filter transmits fluorescent radiation is between 50 and 70 nm.

According to one particularly advantageous embodiment of the invention, the range of wavelengths in which the product of the attenuation of the detector filter and the attenuation of the low-pass filter of the illuminating device leads to an attenuation by a factor of at least $10^6$, extends at least up to the limit detection wavelength of the detector Therefore the range of wavelengths in which the product of detector filter attenuation and low-pass filter attenuation by the illuminating device leads to an attenuation by a factor of at least $10^6$ preferably extends at least up to 1000 nm, and even further preferably up to 1150 nm.

In addition, in the range of wavelengths transmitted by the detector filter, the low-pass filter of the illuminating device exhibits attenuation by a factor of at least $10^6$.

The illuminating device may comprise a light-head placed in position via a hinged arm.

Alternatively, the illuminating device may comprise a headlamp intended to be placed over the surgeon's head.

According to one embodiment, the illuminating device is adapted to provide continuous lighting.

According to another embodiment, the illuminating device is adapted to provide pulsed lighting.

Preferably, the illuminating device comprises light-emitting diodes.

Also, the power of the illuminating device is advantageously 40 kLux or stronger.

The detector may be a CCD or CMOS camera.

According to one particular embodiment, the excitation wavelength is 780 nm and the detector filter transmits radiation in a band between 820 and 850 nm.

According to another embodiment, the excitation wavelength is 750 nm and the detector filter transmits radiation in a band between 780 and 870 nm.

BRIEF DESCRIPTION OF THE DRAWINGS

Other characteristics and advantages of the invention will become apparent from the following detailed description which refers to the appended drawings in which:

FIGS. 7A and 7B give transmission curves of band-pass filters used to filter the detector in some fluorescence imaging devices on the market;

DETAILED DESCRIPTION OF THE INVENTION

Figure 1:
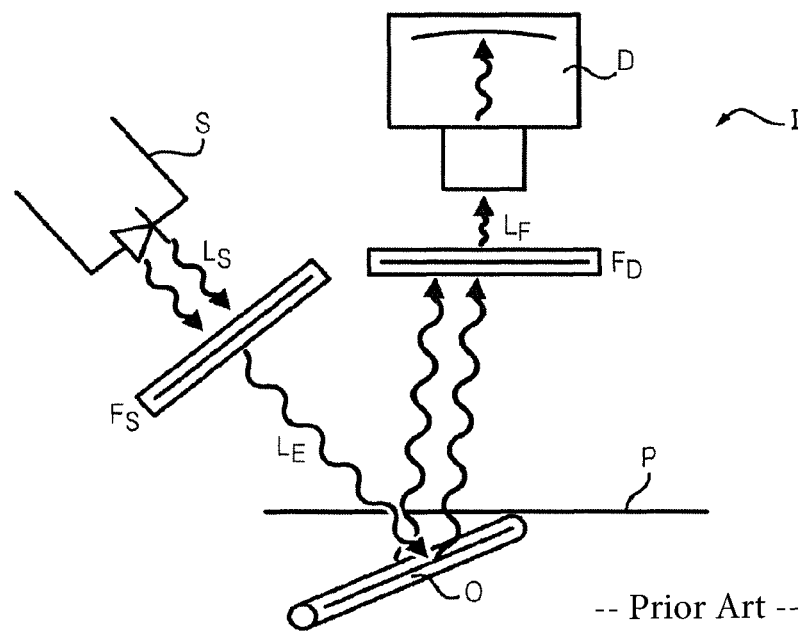
FIG. 1 is a block diagram of the principle of fluorescence imaging.
Figure 2:
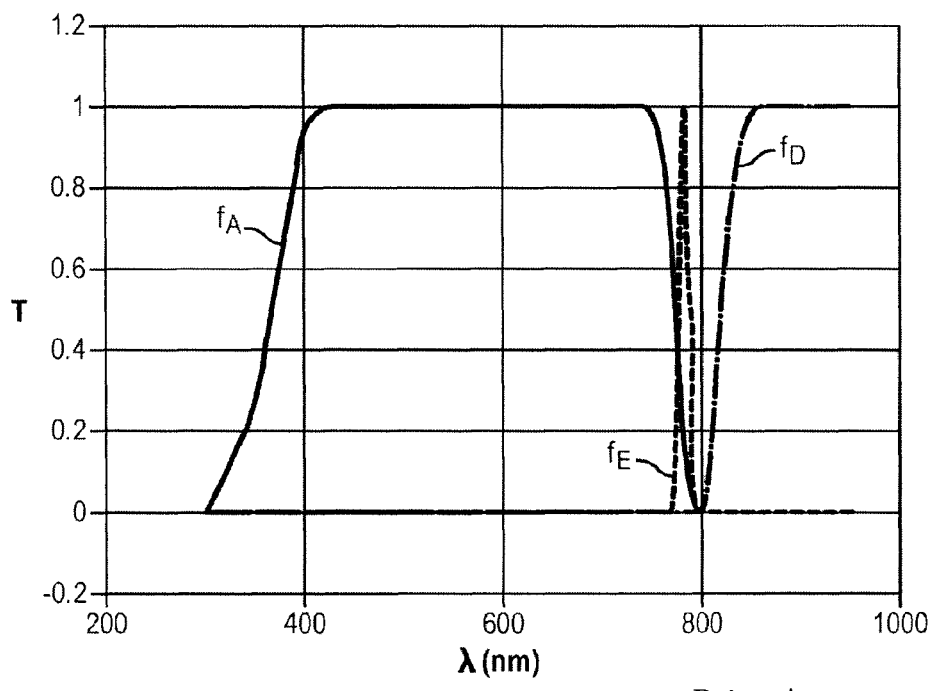
FIG. 2 is a graph showing the principle of filtering ambient light, excitation light and of detector filtering in fluorescence imaging.
Figure 3:
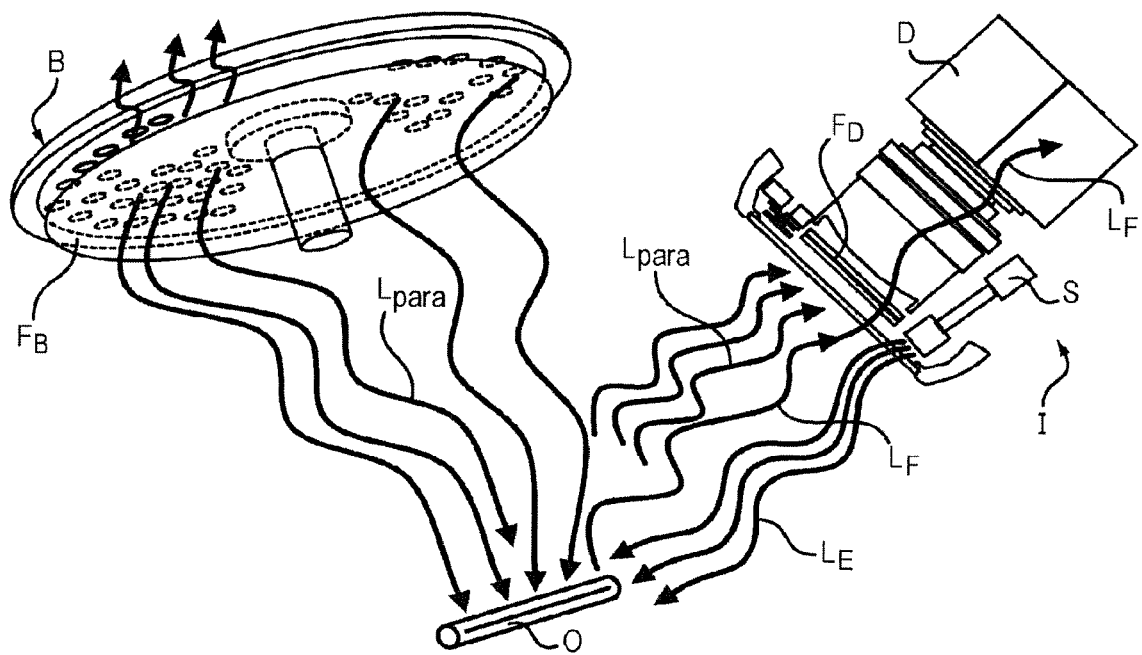
FIG. 3 is a block diagram of an imaging system according to the invention.

FIG. 3 is an overall schematic of the system according to one embodiment of the invention.

This system comprises an operating room illuminating device B and a fluorescence imaging device I directed towards a region O symbolising the part of a patient (human being or animal) of which it is desired to obtain fluorescence images and into which a fluorescent marker is injected for this purpose.

The fluorescence imaging device I is advantageously a device marketed by the Applicant under the trade name Fluobeam™.

This device I comprises a light source S able to emit excitation radiation $L_E$ to excite the fluorescent marker located in or passing through the region O to be observed, in a range of emission wavelengths $L_F$ between 600 and 900 nm, and a detector D adapted to detect the fluorescent radiation $L_F$ emitted by the marker under the effect of excitation by the light source S.

To perform fluorescence measurement, the detector is filtered with a filter $F_D$ which eliminates visible radiation wavelengths which correspond to operating room lighting, whilst allowing the passing of near infra-red wavelengths corresponding to fluorescence.

Figure 7B:
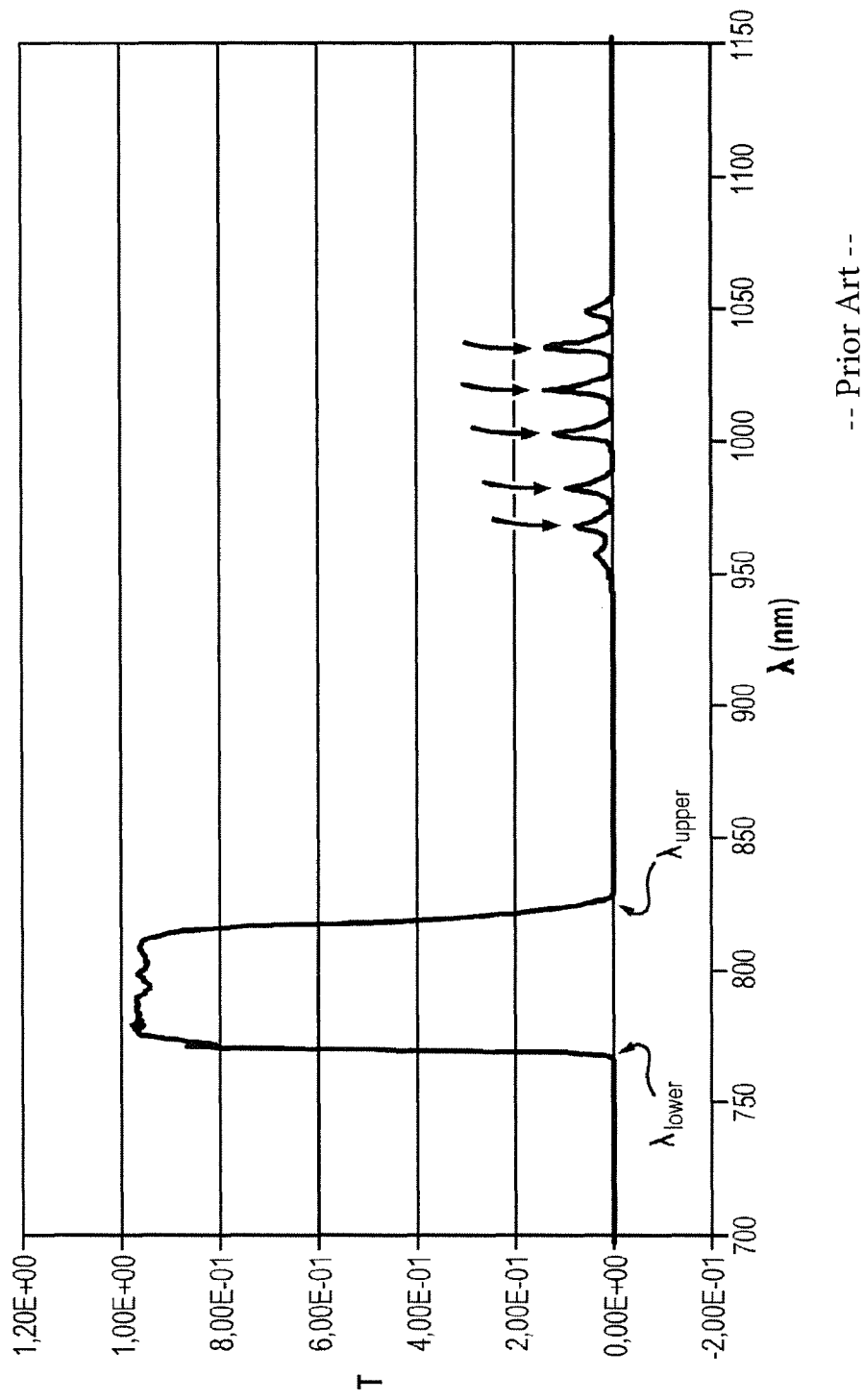

According to one preferred embodiment, the filter of the detector comprises a band-pass filter $F_{D1}$ whose bandwidth lies in the wavelengths of the near infra-red corresponding to fluorescence. An example of a transmission curve of such a band-pass filter is shown in FIGS. 7A and 7B, which are commented on below.

Alternatively, the detector filter may also transmit wavelengths shorter than visible radiation without departing from the scope of the invention. However, for reasons of conciseness the term «band-pass» will be used for these two variants.

The filter $F_D$ may therefore be formed of a combination of filters allowing the desired ranges of attenuation and transmission to be obtained.

According to one embodiment of the invention illustrated in FIG. 3, the operating room illuminating device is a surgical light-head i.e. a light source of large size intended to illuminate the surgical field with white light preventing any shadowing formed for example by the surgeon's head and hands, the instruments used, etc.

It is a very powerful light source (40 kLux or more, often up to 150 kLux).

The NF EN 60601-2-41 standard cited above lays down the requirement of a certain colour temperature range and a certain colour rendering index (CRI).

At the current time, the colour temperature must generally be between 3000 K and 6700 K and the colour rendering index must be between 85 and 100%, preferably in the order of 95%.

A surgical light is typically in the form of a dome having a plurality of lamps.

This dome is generally joined to a hinged arm attached to the ceiling or to any suitable support in the operating room, so that it can be directed towards the operating area to provide the surgeon with lighting having the best possible contrast.

According to another embodiment of the invention (not illustrated) the operating room lighting device is a headlamp intended to be placed over the surgeon's head.

Aside from the fact that the light beam is better focused with such a headlamp than with an overhead surgical light, the constraints related to the quality of lighting (in particular in terms of power, colour temperature and colour rendering index) are the same for these two types of devices.

Therefore the filtering solution of the invention which is described in detail below applies to any operating room illuminating device whether an overhead surgical light or a headlamp.

Current operating room lighting comprises either halogen lamps or light-emitting diodes (LEDs), the latter tending to replace the former.

Figure 4A:
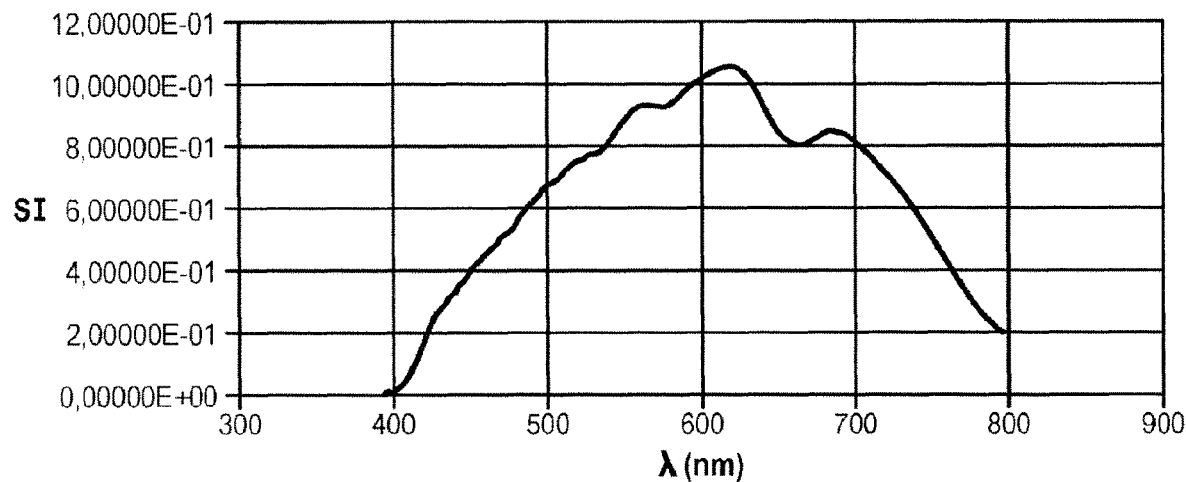
FIGS. 4A and 4B respectively illustrate operating room lighting spectra of halogen lamps and light-emitting diodes.

FIG. 4A shows the spectrum of halogen-type lighting which has a colour rendering index of 91.5, a luminous flux per unit surface area of 66 kLux and colour temperature of 4000 K.

Figure 4B:
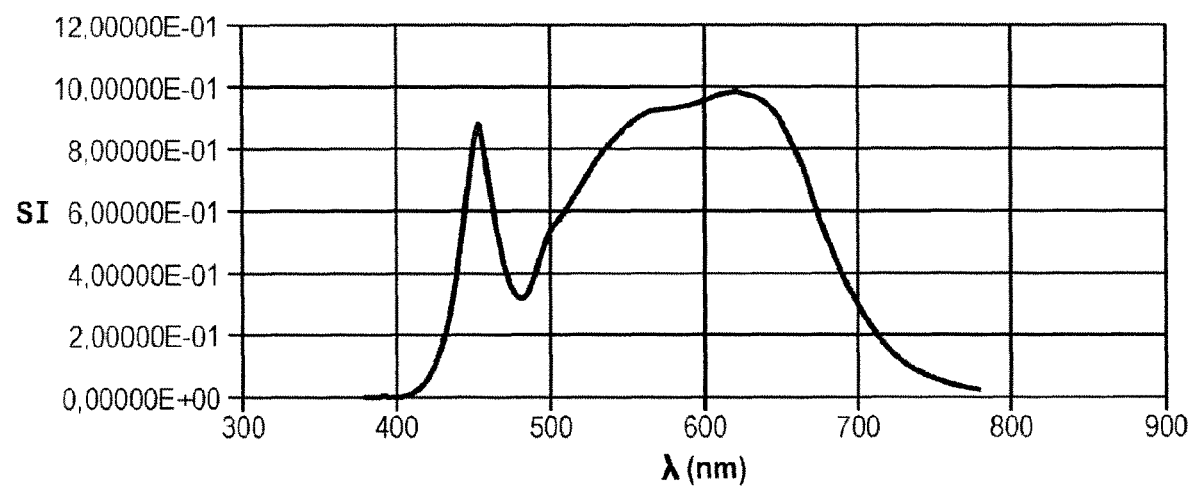

FIG. 4B gives the spectrum of light with light-emitting diodes (LEDs), which has a colour rendering index of 90.5, a luminous flux per unit surface area of 60 kLux and colour temperature of 3719 K.

The comparison between these two spectra shows that the LED lighting provides a much lower light level at wavelengths longer than 700 nm than halogen lighting.

It would therefore be advantageous, in order to conduct fluorescence imaging in the near infra-red in the operating room, to choose LED lighting which allows easier elimination of the infra-red component.

To prevent transmission of infra-red wavelengths of the illuminating device, a low-pass filter $F_B$ is placed in front of it having a cut-off frequency in the order of 700 to 750 nm.

Figure 5:
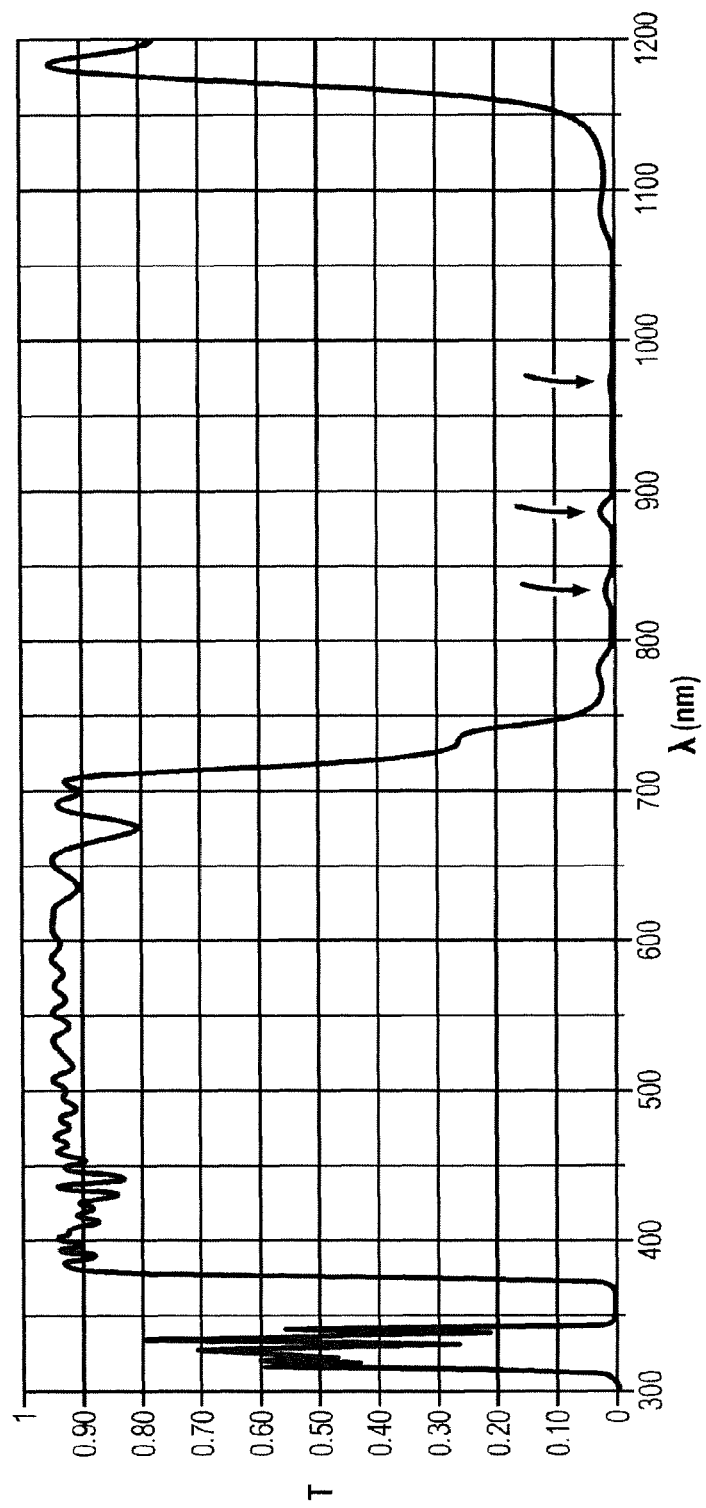
FIG. 5 illustrates the transmission curve of a low-pass filter used in existing operating room lighting and having attenuation bouncing between 800 and 900 nm.

FIG. 5 shows the spectrum of a low-pass interference filter commonly used to cut off the near infra-red from lighting in an operating room.

On account of the large surface area of the illuminating device (typically in the order of 0.5 m$^2$), the technical solution that is economically most reasonable for filtering the lighting of the operating room is the use of a low-cost interference filter.

However attenuation bouncing is observed on this type of filter (designated by arrows) at between 800 and 900 nm, which generate parasitic light in the fluorescence wavelengths.

Such a filter cannot therefore be used for the intended application.

A better performing interference filter in the range of fluorescence wavelengths must therefore be chosen which allows sharp-cut filtering of illumination from an overhead surgical light or headlamp over a wavelength range above 700 or 750 nm, so as not to deteriorate the colour rendering index or at least to obtain possible restoring thereof by adding a red component.

It is within the reach of persons skilled in the art to choose a filter among those on the market which has the required performance level or to have an adequate filter manufactured by a specialised company on the basis of specifications provided.

Figure 6:
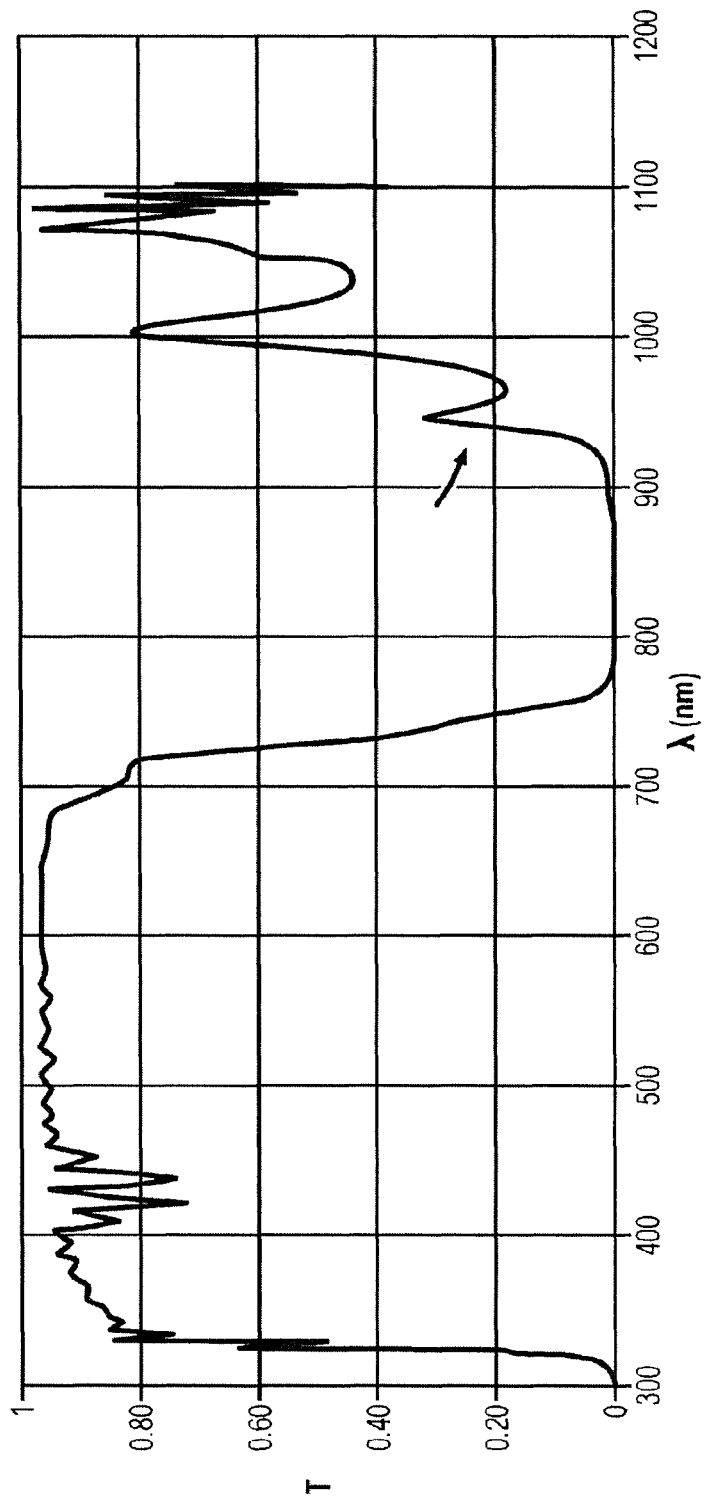
FIG. 6 illustrates the transmission curve of a low-pass filter able to be used to filter operating room lighting.

FIG. 6 shows the spectrum of an interference filter which can be used to filter an overhead surgical light or headlamp to implement the invention.

This filter shows good attenuation between 800 and 900 nm but significant peaking of attenuation (designated by arrows) above 900 nm.

When an overhead surgical light or headlamp is filtered with this type of filter there is therefore parasitic light in the illumination spectrum in the long wavelengths of the near infra-red i.e. around 900 nm.

This parasitic light is designated by the reference $L_{para}$ in FIG. 3.

As will be seen below, this peaking can be offset by low-pass filtering of the detector to cut off the corresponding long wavelengths.

In addition as is known per se the filtering of the detector D generally comprises a band-pass filter $F_{D1}$ designed so that only those photons corresponding to the fluorescence $L_F$ emitted by the marker are detected.

In general, a band-pass width in the order of 50 to 70 nm is appropriate, the value of the lower and upper cut-off wavelengths (respectively denoted $\lambda_{lower}$ and $\lambda_{upper}$) and being selected as a function of the fluorescence emission spectrum of the marker under consideration.

Yet the inventors have found that the band-pass filters used in the devices on the market in fact exhibit attenuation peaking or bouncing at wavelengths between 800 and 1000 nm.

FIG. 7A for example shows the spectrum of a Chroma HQ817-25 filter which is used in the Flare™ and Mini-Flare™ systems for example described above.

Very good attenuation is observed between 850 and 1040 nm, but major bouncing (designated by the arrows) occurs on and after 1050 nm.

FIG. 7B shows the spectrum of a Chroma HQ795/50 filter which is used for example in the SurgOptix system mentioned above.

Very good attenuation is observed between 830 and 940 nm, but significant bouncing (designated by the arrows) at between 950 and 1050 nm.

It is not usual to examine the filter behaviour at wavelengths longer than 900 nm.

It is effectively generally considered that at these wavelengths the sensitivity of the detectors (CCD or CMOS sensors) is low and that the LEDS of the operating room lighting no longer emit.

In addition, in conventional florescence applications, ambient lighting is relatively low-powered which means that the parasitic light at such wavelengths has little influence on the signal measured by the detector.

However, the inventors have ascertained that a detector still has some sensitivity up to 1000 nm, and even higher.

Figure 8A:
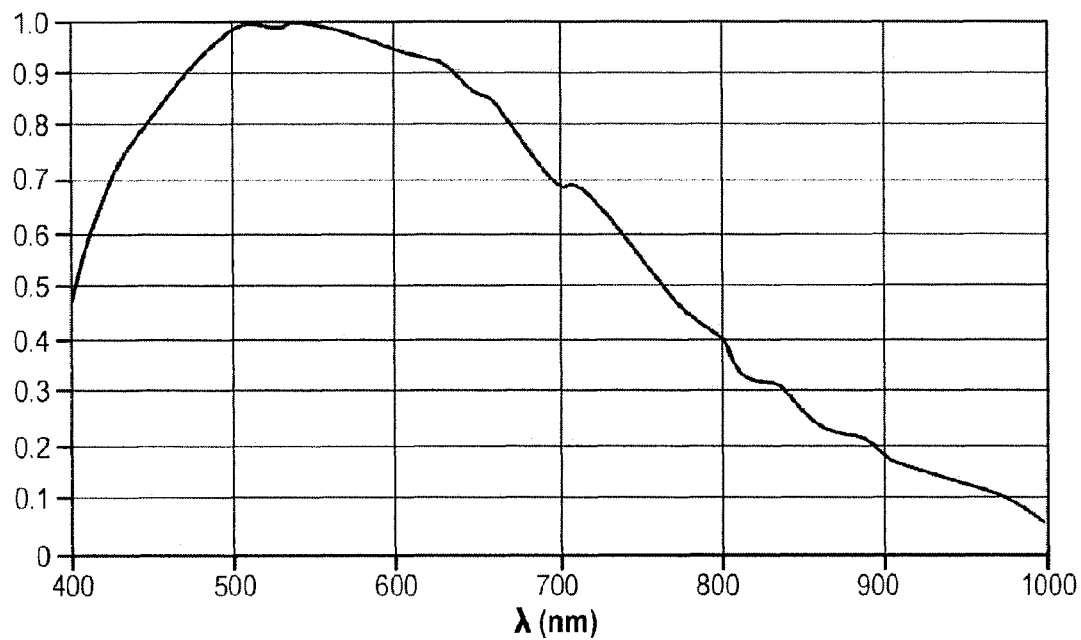
FIG. 8A gives the sensitivity curve of a CCD sensor of the detector as a function of wavelength.

FIG. 8A therefore illustrates the sensitivity as a function of wavelength of a CCD sensor typically used in a fluorescence imaging device such as the Fluobeam™ device.

Figure 8B:
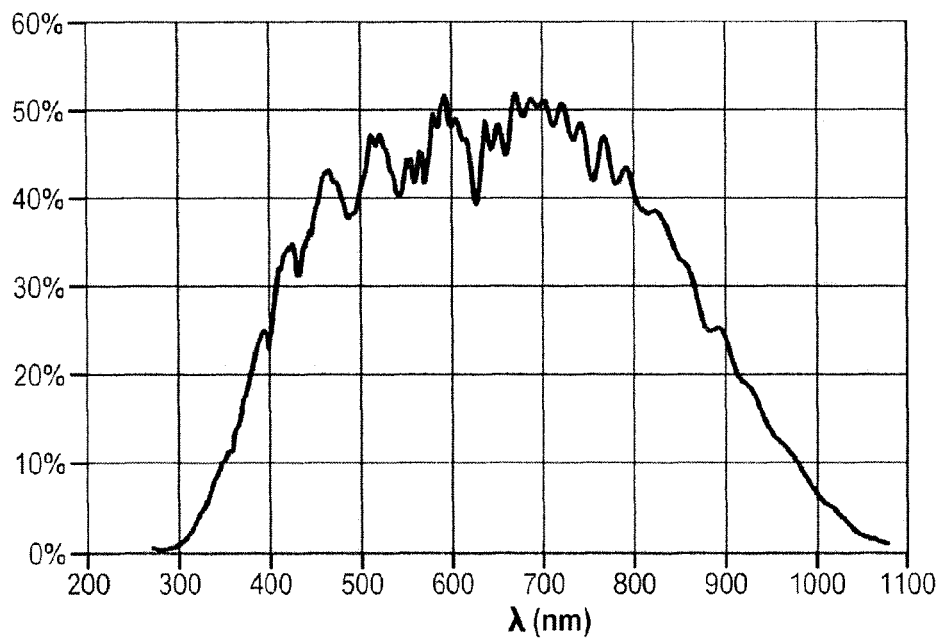
FIG. 8B gives the quantum efficiency curve of a CMOS sensor of the detector as a function of wavelength.

FIG. 8B illustrates the quantum efficiency (QE) as a function of wavelength of a CMOS sensor which could also be used in the fluorescence imaging device.

These types of sensors exhibit high sensitivity at visible wavelengths and lower but still significant sensitivity at wavelengths corresponding to the near infra-red.

Although this sensitivity is low, insofar as the lighting provided by the operating room device is very powerful (possibly reaching 150 kLux), the parasitic light—resulting from poor attenuation by the low-pass filter of the overhead surgical light or headlamp and the band-pass filter of the detector—is sufficiently strong to produce significant background noise in the fluorescence signal measured by the sensor.

On the basis of these considerations, an intuitive approach would be to improve the filtering of the operating room illuminating device.

It can effectively be considered that if it were given proper use, the filtering would allow all parasitic photons to be eliminated at the source. The detector would therefore only detect the fluorescence photons, in particular those corresponding to the longest wavelengths.

However, as indicated above, having regard to the surface area of the operating room illuminating device (in the order of 0.5 m$^2$ for an overhead surgical light) the cost of an adequate filter would be prohibitive.

Also, even if this solution would allow greater photon detection, these photons are few in number and the sensitivity of the detector at the corresponding wavelengths is low.

Finally the adding of an additional filter would risk modifying the colour rendering index and the colour temperature of the operating room lighting.

On the contrary, the inventors have chosen to apply an additional filter to the detector, despite the loss of photons detectable by the detector, thereby going against preconceived opinion according to which an additional filter would lead to reduced quality of the signal measured by the detector.

It could effectively be feared that by further filtering the detector an insufficient number of photons would be detected to provide images having sufficient contrast.

The additional filtering of the detector is formed of a low-pass filter which, above the cut-off wavelength, exhibits very strong attenuation.

In other words, the filter $F_D$ of the detector D comprises a band-pass or high-pass filter $F_{D1}$ (cf. FIG. 9c) combined with a low-pass filter $F_{D2}$ (cf. FIG. 9b) which transmits the wavelengths of the near infra-red to be detected by the detector and in which, above its upper cut-off wavelength $\lambda_{max}$, the product of the attenuations of the filter of the operating room illuminating device and of the detector filter leads to an attenuation by a factor of at least $10^6$.

This condition must preferably be heeded at least up to the detection limit of the detector D.

Figure 9:
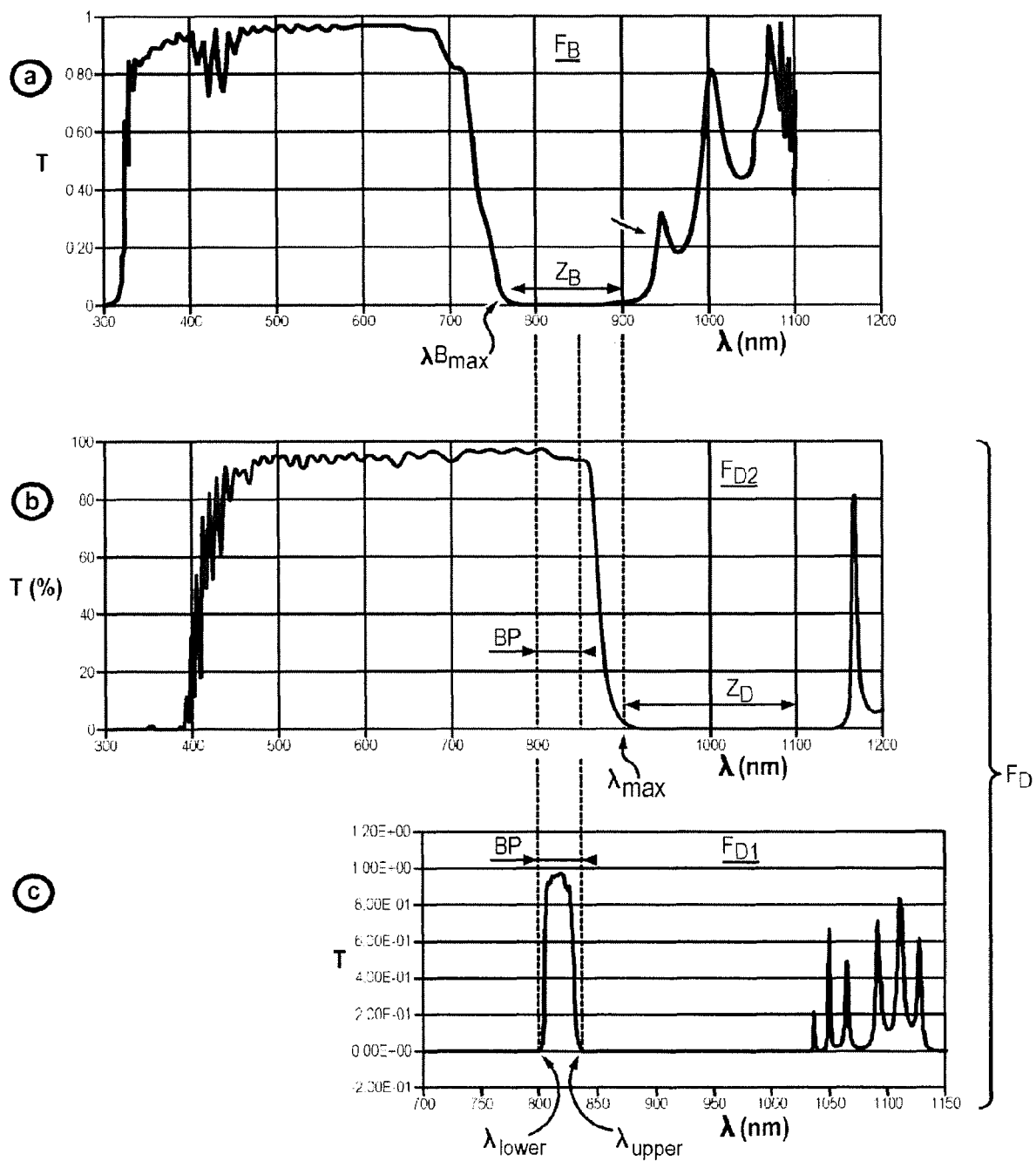
FIGS. 9a to 9c respectively illustrate the transmission curves of the low-pass filter in operating room lighting, of the low-pass filter of the detector in one embodiment of the invention, and of the band-pass filter of the detector.

The range of wavelengths concerned by this drastic attenuation is schematised by the zone $Z_D$ in FIG. 9b, which simultaneously shows the transmission curves of the filter of the operating room lighting (FIG. 9a corresponding to FIG. 6 described above), of an example of an additional low-pass filter $F_{D2}$ suitable for the detector (FIG. 9b), and of an example of a band-pass filter $F_{D1}$ of the detector (FIG. 9c, corresponding to FIG. 7A commented on above).

Evidently the transmission curves shown here are solely illustrative, and persons skilled in the art may vary the characteristics of transmission and cut-off wavelengths in relation to the specificities of the operating room lighting and of the imaging device under consideration.

Regarding the choice of filter for the operating room illuminating device, care must also be taken to ensure that the low-pass filter $F_B$ of the overhead surgical light or headlamp does not transmit any wavelength to be measured by the detector (in other words the cut-off wavelength $\lambda_{Bmax}$ of the low-pass filter $F_B$ is shorter than the lower cut-off wavelength $\lambda_{lower}$ of the band-pass filter $F_{D1}$ whose band-pass width BP lies within zone $Z_B$ in FIG. 9a, corresponding to attenuation of the operating room lighting by a factor of at least $10^6$, preferably at least $10^7$) and to ensure that the attenuation peaking or fluctuations of the low-pass filter $F_B$ of the overhead surgical light or headlamp only occur at wavelengths above the band-pass width BP of the detector filter.

As illustrated in FIGS. 9a and 9b, the peaking of the low-pass filter $F_B$ of the overhead surgical light or headlamp starts at a wavelength above the bandwidth BP of the detector but since it lies above the cut-off frequency $\lambda_{max}$, this peaking is attenuated by the filter $F_{D2}$ (zone ZD in FIG. 9b).

In FIG. 9b it can be seen that the additional filter $F_{D2}$ of the detector shows strong peaking at around 1200 nm; however this wavelength is longer than the limit detection wavelength of the detector which means that this peaking has no incidence on the quality of images.

It is within the reach of persons skilled in the art to choose a filter among the filters on the market which have the required performance level or to have manufactured an adequate filter by a specialised company on the basis of specifications for detector filtering.

The inventors have surprisingly verified that the quality of the images and the separation between the different structures is distinctly improved with this additional filtering of the detector.

In particular, they observed that this additional filtering allowed elimination of bias and background noise which masked the fluorescence photons derived from deep regions, and which are therefore few in number.

The detector filtered in this manner is more sensitive to the fluorescence signal originating from the deep layers and produces more contrasted images.

In addition, since the surface area of the detector is much smaller than that of an overhead surgical light, the use of a high performance filter to obtain attenuation by a factor of more than $10^6$ at longer wavelengths does not penalise the system financially.

As a non-limiting illustration, in a first embodiment the Fluobeam™ device marketed by the Applicant has an excitation wavelength of 780 nm and a bandwidth of the band-pass filter $F_D$ of between 820 and 850 nm; in a second embodiment, the excitation wavelength is 750 nm and the bandwidth of the band-pass filter $F_D$ is between 780 and 870 nm.

Evidently the numerical values given above are solely illustrative and those skilled in the art, as a function of the filters available and the fluorescence wavelengths to be detected, are able to develop adequate filters for the operating room lighting and for the detector.

Experimental Results

Surgical procedure was performed on the heart of an animal using the system described above and under the same experimental conditions, with the exception in the second case that the additional filtering of the detector described above was added (the transmission curve of which is given in FIG. 9b).

Figure 10A:
FIGS. 10A and 10B are fluorescence images respectively obtained with filtering system of the detector in the prior art and with a system conforming to the invention.
Figure 10B:

FIGS. 10A and 10B are fluorescence images of the heart recorded after injection of indocyanine green (ICG), with and without the additional low-pass filter of the detector respectively.

It is observed that with the system conforming to the invention many more deep-lying blood vessels can be seen.

Figure 11:
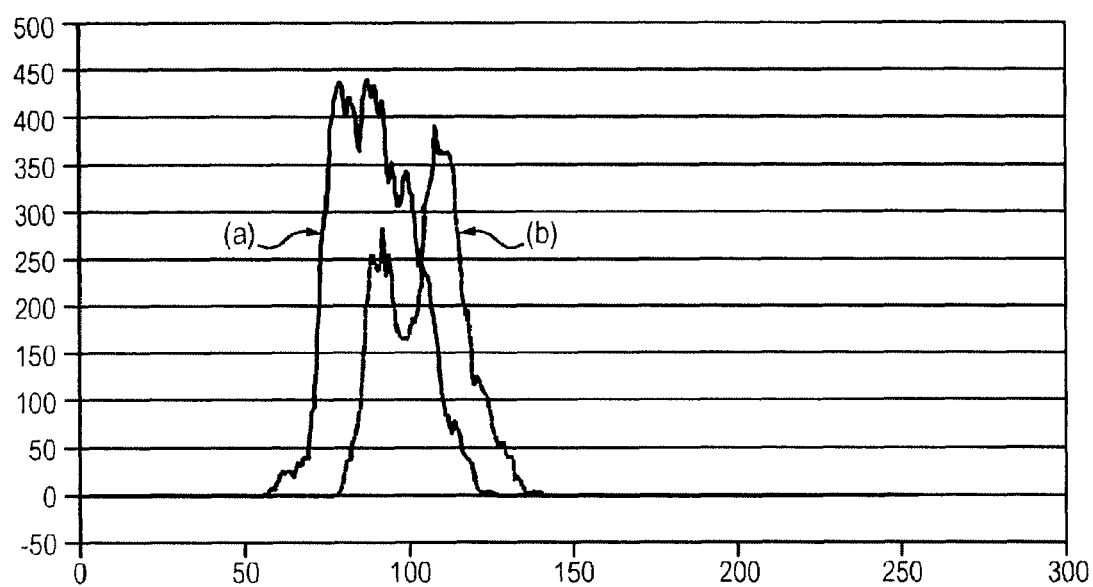
FIG. 11 gives histograms respectively obtained with a filtering system of the detector in the prior art and with a system conforming to the invention.

This result can also be observed in FIG. 11 which gives a histogram obtained in a region outside the coronaries, without (curve (a)) and with (curve (b)) the additional low-pass filter of the detector.

In this histogram one of the modes corresponds to the surface of the heart and the other to the deep vessels.

A comparison between these two curves clearly shows that the bimodal appearance of the histogram is much stronger in the image acquired with the additional low-pass filter of the detector than the image acquired without this filter.

It therefore follows that the additional filter substantially increases the contrast of the deep vessels.

REFERENCES

[1] S. Gioux, H. S. Choi et J. F. Frangioni, «Image-Guided Surgery Using Invisible Near-Infrared Light: Fundamentals of Clinical Translation,» *Molecular Imaging*, vol. 9, n° 15, pp. 237-255.

[2] S. L. Troyan, V. Kianzad, S. L. Gibbs-Strauss, S. Gioux, A. Matsui, R. Oketokoun, L. Ngo, A. Khamene, F. Azar et J. V. Frangioni, «The FLARE™ Intraoperative Near-Infrared Fluorescence Imaging System: A First-in-Human Clinical Trial in Breast Cancer Sentinel Lymph Node Mapping,» *Ann Surg Oncol*, vol. 16, pp. 2943-2952, 2009.

[3] J. S. D. Mieog, S. S. Troyan, M. Hutteman, K. J. Donohoe, J. R. van der Vorst, A. Stockdale, G.-J. Liefers, H. S. Choi, S. L. Gibbs-Strauss, H. Putter, S. Gioux, P. J. Kuppen, Y. Ashitate, C. W. Löwik, V. T. Smit, R. Oketokoun, L. H. Ngo, C. J. van de Velde, J. V. Frangioni et A. L. Vahrmeijer, «Toward Optimization of Imaging System and Lymphatic Tracer for Near-Infrared Fluorescent Sentinel Lymph Node Mapping in Breast Cancer,» *Ann Surg Oncol*, vol. 18, pp. 2483-2491, 2011.

[4] G. Themelis, J. S. Yoo, K.-S. Soh, R. Schulz et V. Ntziachristos, «Real-time intraoperative fluorescence imaging system using light-absorption correction,» *Journal of Biomedical Optics*, vol. 14, n° %16, 2009.

The invention claimed is:

1. A fluorescence imaging system for an operating room, said system comprising:
   an operating room illuminating device capable of emitting white light and
   a fluorescence imaging device,
   said fluorescence imaging device comprising:
      a light source capable of emitting excitation radiation in a range of wavelengths of between 600 and 900 nanometers to excite a fluorescent marker;
      a detector adapted to detect the fluorescent radiation emitted by the marker under the effect of the excitation by the light source; and
      a filter of the detector comprising a first detector filter and a second detector filter, the second detector filter being a band-pass filter or high-pass filter and being adapted to block the excitation radiation and to transmit to the detector those photons having a wavelength included in the range of wavelengths of fluorescent radiation emitted by the marker, the first detector filter being a first low-pass filter having a first upper cut-off wavelength,
   the system further comprising:
   a second low-pass filter placed in front of the illumination device and having a second upper cut-off wavelength that is below the emission range of the fluorescent marker, said second low-pass filter nonetheless being able to exhibit attenuation peaking or fluctuations at wavelengths above the emission range of the fluorescent marker,
   wherein in a range of wavelengths extending from the upper cut-off wavelength and through the wavelengths which the attenuation peaking or fluctuations of the second low-pass filter are observed, the product of attenuation by the filter of the detector and the second low-pass filter leads to an attenuation by a factor of at least $10^6$.

2. The system of claim 1, wherein the wavelength of excitation radiation is between 630 and 810 nanometers.

3. The system of claim 1, wherein the bandwidth in which the filter of the detector transmits fluorescent radiation is between 50 and 70 nanometers.

4. The system of claim 1, wherein the range of wavelengths, in which the product of attenuation by the detector filter and of attenuation by the second low-pass filter leads to the attenuation by the factor of at least $10^6$, extends at least as far as the limit detection wavelength of the detector.

5. The system of claim 1, wherein the range of wavelengths, in which the product of attenuation by the filter of the detector and of attenuation by the second low-pass filter leads to the attenuation by the factor of at least 106, extends at least as far as 1000 nanometers.

6. The system of claim 1, wherein in the range of wavelengths transmitted by the detector filter, the second low-pass filter exhibits attenuation by a factor of at least 106.

7. The system of claim 1, wherein the illuminating device comprises a dome-shaped light-head which can be positioned via a hinged arm.

8. The system of claim 1, wherein the illuminating device comprises a headlamp.

9. The system of claim 1, wherein the illuminating device is adapted to provide continuous lighting.

10. The system of claim 1, wherein the illuminating device is adapted to provide pulsed lighting.

11. The system of claim 1, wherein the illuminating device comprises light-emitting diodes.

12. The system of claim 1, wherein the power of the illuminating device is 40 k-Lux or higher.

13. The system of claim 1, wherein the detector is a CCD or CMOS camera.

14. The system of claim 1, wherein the excitation wavelength is 780 nanometers and wherein the filter of the detector transmits radiation in a band between 820 and 850 nanometers.

15. The system of claim 1, wherein the excitation wavelength is 750 nanometers and wherein the filter of the detector transmits radiation in a band between 780 and 870 nanometers.

* * * * *